US012194177B2

(12) United States Patent
Mason et al.

(10) Patent No.: US 12,194,177 B2
(45) Date of Patent: Jan. 14, 2025

(54) SYSTEMS AND METHODS FOR DELIVERING CHLORINE DIOXIDE USING A LIQUID CURTAIN

(71) Applicant: Sabre IP Acquistionco, LLC, New York, NY (US)

(72) Inventors: John Y. Mason, Slingerlands, NY (US); Von Christopher Davis, Columbia, MO (US); Julian Noah Rosenberg, Altamont, NY (US)

(73) Assignee: Sabre IP Acquistionco, LLC, New York, NY (US)

( * ) Notice: Subject to any disclaimer, the term of this patent is extended or adjusted under 35 U.S.C. 154(b) by 755 days.

(21) Appl. No.: 17/428,573

(22) PCT Filed: Feb. 5, 2020

(86) PCT No.: PCT/US2020/016803
§ 371 (c)(1),
(2) Date: Aug. 4, 2021

(87) PCT Pub. No.: WO2020/163483
PCT Pub. Date: Aug. 13, 2020

(65) Prior Publication Data

US 2022/0105215 A1 Apr. 7, 2022

Related U.S. Application Data

(60) Provisional application No. 62/801,560, filed on Feb. 5, 2019.

(51) Int. Cl.
*A61L 2/18* (2006.01)
*A01N 59/00* (2006.01)
*A01P 1/00* (2006.01)
*A61L 2/26* (2006.01)

(52) U.S. Cl.
CPC ................ *A61L 2/18* (2013.01); *A01N 59/00* (2013.01); *A01P 1/00* (2021.08); *A61L 2/26* (2013.01); *A61L 2202/15* (2013.01)

(58) Field of Classification Search
CPC . A61L 2/18; A61L 2/183; A61L 2/186; A61L 2/24; A61L 2/26; A61L 2202/15; A01P 1/00; A01N 59/00; A22C 21/0061
See application file for complete search history.

(56) References Cited

U.S. PATENT DOCUMENTS 5,843,531 A * 12/1998 Klett ........................ D06B 1/06 427/420
2004/0101438 A1 * 5/2004 Nelson .................... B65B 55/10 422/1
2012/0225173 A1 * 9/2012 Larson ..................... A23B 4/16 99/485

* cited by examiner

*Primary Examiner* — Timothy C Cleveland
(74) *Attorney, Agent, or Firm* — FOLEY HOAG LLP

(57) ABSTRACT

Provided herein are methods and systems for applying chlorine dioxide comprising contacting a target surface with a curtain of a liquid chlorine dioxide treatment solution. The disclosed methods and systems provide improved delivery of chlorine dioxide to target surfaces and have the advantages of providing improved treatment efficacy, improved safety, and reduced chemical usage. The methods and systems can be used for treatment of a variety of surfaces in need of decontamination, including but not limited to food products.

27 Claims, 7 Drawing Sheets

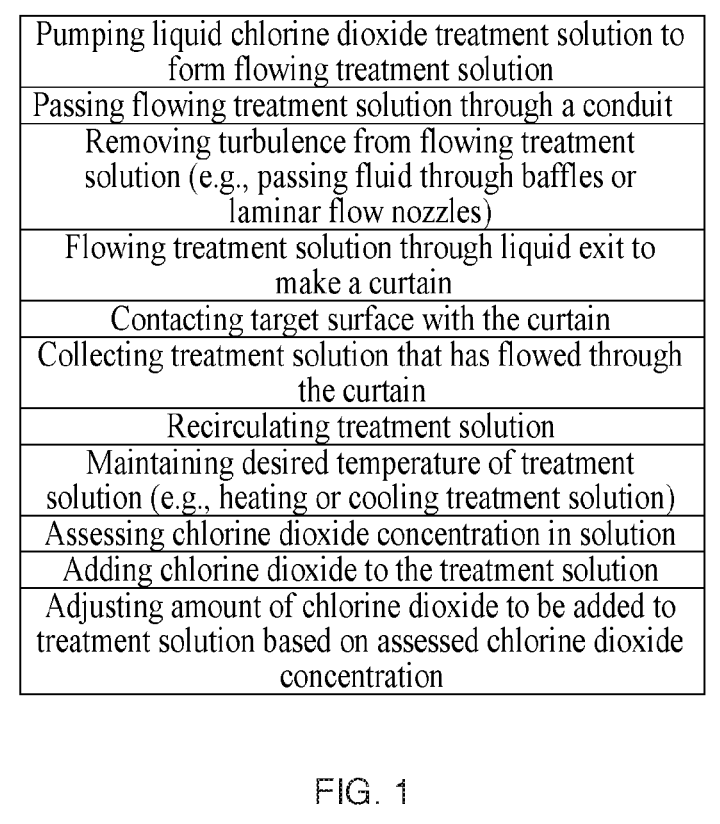

| |
|---|
| Pumping liquid chlorine dioxide treatment solution to form flowing treatment solution |
| Passing flowing treatment solution through a conduit |
| Removing turbulence from flowing treatment solution (e.g., passing fluid through baffles or laminar flow nozzles) |
| Flowing treatment solution through liquid exit to make a curtain |
| Contacting target surface with the curtain |
| Collecting treatment solution that has flowed through the curtain |
| Recirculating treatment solution |
| Maintaining desired temperature of treatment solution (e.g., heating or cooling treatment solution) |
| Assessing chlorine dioxide concentration in solution |
| Adding chlorine dioxide to the treatment solution |
| Adjusting amount of chlorine dioxide to be added to treatment solution based on assessed chlorine dioxide concentration |

FIG. 1

SYSTEMS AND METHODS FOR DELIVERING CHLORINE DIOXIDE USING A LIQUID CURTAIN

RELATED APPLICATIONS

This application is the U.S. National Stage of International Application No. PCT/US2020/016803, filed Feb. 5, 2020, which designates the U.S., published in English, and claims the benefit of U.S. Provisional Application No. 62/801,560, filed on Feb. 5, 2019. The entire teachings of the above applications are incorporated herein by reference.

BACKGROUND

Liquid solutions containing chlorine dioxide or other disinfecting chemicals are most frequently applied by spraying to contact a target surface. Spraying and similar application methods break the liquid treatment solution from a bulk volume into water droplets (e.g., droplets in the form of a mist or aerosol). Applicant has found that when such methods are employed with liquid chlorine dioxide treatment solutions, a very substantial amount of the chlorine dioxide that was originally present in the solution escapes into the air. The escape, or off-gassing, of chlorine dioxide reduces the amount of chlorine dioxide remaining in the treatment solution, resulting in loss of chemical and failure of chlorine dioxide to reach the intended target. The off-gassing also poses significant hazards, including environmental and health hazards, such as inhalation hazard.

The present disclosure provides alternative, more efficient approaches for application of chlorine dioxide that remedy these issues. The methods improve delivery of chlorine dioxide to a target surface. The methods offer advantages including improved treatment efficacy, improved safety, and reduced chemical usage.

BRIEF DESCRIPTION OF THE DRAWINGS

FIG. 1 depicts steps that can be included in embodiments of the methods disclosed herein.

FIG. 3A shows an edge of a trough (the trough being a conduit for treatment solution to flow towards the liquid exit) as a liquid exit that can be used to form a curtain. FIG. 3B shows a downwardly sloping lip on the edge of a trough (the trough being a conduit for treatment solution to flow towards the liquid exit) as a liquid exit that can be used to form a curtain. FIG. 3C shows that a liquid exit can also be connected to a curved surface of a conduit (e.g., a trough) from which liquid falls to form a curtain. FIG. 3D shows that a liquid exit can also be an opening between two parallel surfaces.

FIG. 4A shows a conduit 400 including a baffle system 410 having surfaces 420 in serpentine (when viewed cross-sectionally) arrangement (e.g., parallel to each other) around which fluid flows towards a liquid exit 430; such a system can also include parallel surfaces through which fluid flows before it drops to form a curtain. FIG. 4B shows a conduit 450 including a baffle system 460 having intersecting surfaces 470 in X-shape (when viewed cross-sectionally) arrangement, the surfaces having openings 480 through which fluid flows towards a liquid exit 480; such a system can also include parallel surfaces through which fluid flows before it drops to form a curtain.

SUMMARY OF THE INVENTION

Figure 2A:
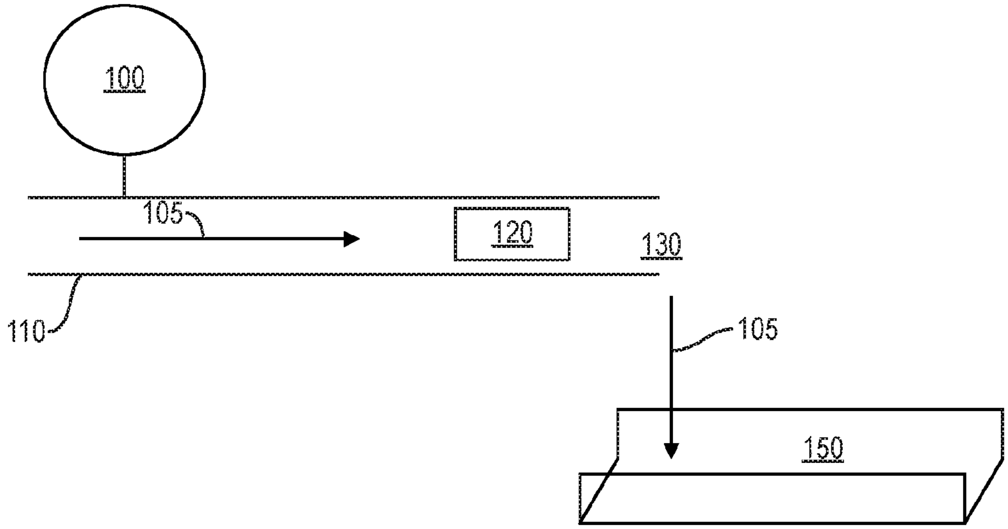
FIG. 2A depicts components of an embodiment of a system disclosed herein.

In one aspect, the disclosure provides a method comprising forming stable curtain of a liquid chlorine dioxide treatment solution that flows downward under gravity from a liquid exit onto a target surface (e.g., a surface in need of decontamination).

In some embodiments, the method comprises flowing the liquid chlorine dioxide treatment solution through one or more baffles or laminar nozzles. In some embodiments, passing the liquid chlorine dioxide solution through such baffles or laminar nozzles achieves laminar flow. In some embodiments, the liquid chlorine dioxide treatment solution flows through the one or more baffles or laminar nozzles before it flows from the liquid exit.

In some embodiments, liquid chlorine dioxide treatment solution that contacts the target surface retains at least 70% of the chlorine dioxide concentration that is present in the treatment solution that flows from the liquid exit. In some embodiments, the method comprises maintaining the liquid chlorine dioxide treatment solution at a temperature of at least 100° F.

In some embodiments, the liquid chlorine dioxide treatment solution is at least 30° F. warmer than the ambient temperature.

In another aspect, the disclosure provides a method comprising (i) forming a curtain of a liquid chlorine dioxide treatment solution that flows downward under gravity, and (ii) contacting a target surface with the curtain.

In some embodiments, the method comprises passing the liquid chlorine dioxide treatment solution through one or more baffles or laminar nozzles to achieve laminar flow.

In some embodiments, liquid chlorine dioxide treatment solution that contacts the target surface retains at least 70% of the chlorine dioxide concentration that is present in treatment solution at the location where it first forms the curtain.

In some embodiments, the method comprises maintaining the liquid chlorine dioxide treatment solution at a temperature of at least 100° F.

In some embodiments of these methods, the liquid chlorine dioxide treatment solution is at least 30° F. warmer than the ambient temperature.

The methods disclosed herein can comprise recirculation. For example, liquid chlorine dioxide solution that flows through a liquid curtain can be collected and recirculated through the curtain. In some embodiments, chlorine dioxide is added to liquid chlorine dioxide solution used in the methods.

DETAILED DESCRIPTION OF THE INVENTION

As used herein, singular terms such as "a," "an," or "the" are intended to encompass the plural, unless the context clearly indicates otherwise.

As used herein "ambient temperature" refers to the air temperature (or temperature of any other surrounding atmosphere) in the place (e.g., the room or area) where the method is performed or where the apparatus is used.

As used herein, a "curtain" refers to a sheet of flowing liquid. The sheet can be, e.g., planar or curved.

As used herein, the "height" of a curtain refers to the shortest vertical distance from the top of the curtain (typically this is where chlorine dioxide treatment solution drops from a liquid exit to form the curtain) to the bottom of the curtain (this is where the curtain contacts a conveyor belt or other surface that supports an object to be treated with the curtain, or if no such surface is present, where the curtain contacts a collecting conduit or container). If a curtain flows vertically (vertically means, as is conventional, toward the center of the earth and parallel to the earth's gravitational field) throughout its length, its length is equivalent to its height.

As used herein, the "depth" of a curtain refers to its thickness (or average thickness, if the thickness is not constant throughout). The thickness can be measured by determining the shortest distance from any point on the surface (e.g., the planar or curved surface) of the sheet of flowing liquid to the closest point on the opposite surface (e.g., the planar or curved surface) of the sheet of flowing liquid. Typically, the thickness of the curtain is constant or essentially constant throughout. If the thickness varies, the depth can be determined based on the average thickness as measured at a plurality of points distributed throughout the surface of the curtain.

As used herein, the "length" of a curtain refers to the total distance from where the curtain forms to where the curtain contacts a conveyor belt or other surface that supports an object to be treated with the curtain, or if no such surface is present, where the curtain contacts a collecting conduit or container.

As used herein, the "percent," "percentage" or "%" concentration of a component is intended to refer to the w/w % concentration unless the context indicates otherwise.

As used herein and in the art, "ppm" refers to parts per million. In the describing liquid solutions containing chlorine dioxide or other agents, the present specification employs the term "ppm" to refer to parts per million by weight.

As used herein, a "stable curtain" or "stable sheet" refers to a sheet of flowing liquid that contains no ruptures characterized by the appearance of expanding holes.

As used herein, the "width" of a curtain refers to its average width.

A description of example embodiments of the invention follows. The teachings of all patents, published applications and references cited herein are incorporated by reference in their entirety.

Improved Chlorine Dioxide Retention and Delivery

Applicant has found that the use of spraying and similar methods (that result in the formation of droplets, mists, or aerosols) that are most commonly used for application of liquid chlorine dioxide treatment solutions leads to a loss of very substantial amounts of chlorine dioxide (e.g., 40%, 50%, 60%, 70% or more of the chlorine dioxide that is initially present) into the surrounding atmosphere. This off-gassing of chlorine dioxide wastes chemical and poses risks to humans and non-target objects in the environment (e.g., risks to humans such as inhalation hazard and eye irritation, and risks to non-target objects such as oxidation and/or bleaching). The methods and systems disclosed herein provide improved delivery of chlorine dioxide to a target surface and concomitantly reduce such risks. In some embodiments of the methods and systems, the treatment solution that contacts a target surface retains at least 70%, 75%, 80%, 85% or 90% of the chlorine dioxide concentration that is initially present in treatment solution.

The present disclosure provides improved methods of applying a chlorine dioxide treatment solution to a target surface. In some embodiments, the methods comprise forming a curtain of a liquid chlorine dioxide treatment solution that flows onto a target surface. In some embodiments, the methods comprise contacting a target surface with a curtain of liquid chlorine dioxide treatment solution.

In some embodiments, a method disclosed herein comprises some or all steps disclosed in FIG. 1. In one aspect provided herein is a method comprising (i) pumping liquid chlorine dioxide treatment solution to form flowing treatment solution, (ii) passing flowing treatment solution through a (first) conduit, (iii) removing turbulence from flowing treatment solution and/or creating laminar flow in flowing treatment solution (e.g., by passing flowing treatment solution through baffles or laminar flow nozzles, which may be located within the conduit), (iv) directing flowing treatment solution such that it flows from a liquid exit to make a curtain (e.g., a stable curtain), (v) contacting a target surface with the curtain and (vi) collecting treatment solution that has flowed through the curtain. In some embodiments, the method comprises recirculating treatment solution by directing collected treatment solution back into the first conduit. In some embodiments, collected treatment solution is discarded (e.g., drained away).

In some embodiments, the methods comprise maintaining a desired temperature of the treatment solution, e.g., heating the treatment solution to a temperature disclosed herein.

In some embodiments, the methods comprise adding chlorine dioxide to the treatment solution.

In some embodiments, the methods comprise assessing a chlorine dioxide concentration in treatment solution flowing (e.g., recirculating) through the system.

In some embodiments, the methods comprise adjusting the amount of chlorine dioxide added to the treatment solution (if and to the extent needed) based on the assessed concentration of chlorine dioxide.

Curtain

Methods disclosed herein can comprise forming a curtain of a liquid chlorine dioxide treatment solution that flows (e.g., falls) onto a target surface and/or contacting a target surface with a curtain of liquid chlorine dioxide treatment solution.

Generally, the curtain is a substantially solid sheet of flowing liquid, as opposed to a "rain curtain" or curtain of droplets. In some such embodiments, the substantially solid sheet breaks into droplets along its lateral edges, whereas the inner portion of the sheet contains no ruptures characterized by the appearance of expanding holes.

In some embodiments, the treatment solution flows from a liquid exit to form the curtain. Non-limiting examples of liquid exits are shown in FIG. 3A to 3D. In some embodiments, the liquid exit is the edge of a trough from which the treatment solution falls to form the curtain (see, e.g., FIG. 3A). In some embodiments, the liquid exit is a downwardly sloping surface (e.g., a downwardly sloping curved or flat surface) from which treatment solution flows to form the curtain. In some embodiments, the liquid exit is a downwardly sloping lip, e.g., a downwardly sloping lip along the edge of a trough (see, e.g., FIGS. 3B and 3C). In some embodiments, the liquid exit is an opening from which the treatment solution falls (see, e.g., FIG. 3D). In some such embodiments, the liquid treatment solution passes between two parallel surfaces and then drops from the edge of the lower surface (see, e.g., FIG. 3D).

In some embodiments a method disclosed herein comprises flowing (e.g., pumping) the liquid chlorine dioxide treatment solution through one or more baffles or laminar nozzles to achieve transitional or laminar flow. The laminar flow stream can then be used to form the curtain.

Figure 4A:
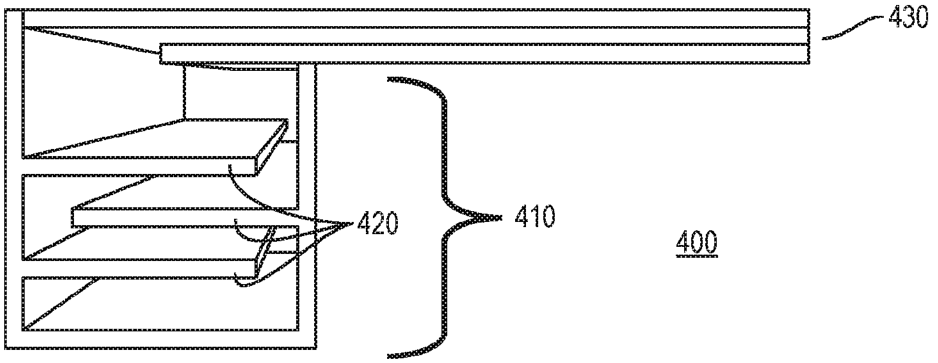
FIG. 4A and FIG. 4B show examples of baffle systems.
Figure 4B:
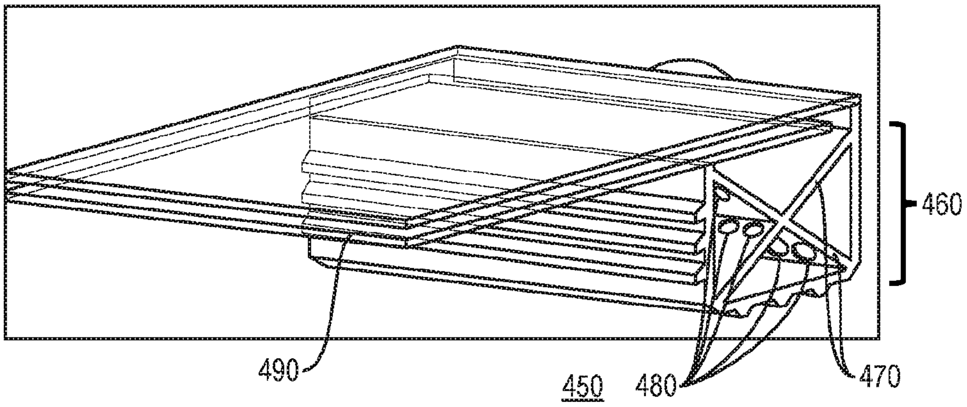

Baffle systems that can be used to achieve laminar flow and form stable curtains (e.g., X baffles and other baffle systems, as shown in FIG. 4B and FIG. 4A) are commercially available and are marketed for forming waterfalls for decorative purposes, as in swimming pool and spa applications.

In some embodiments a method disclosed herein comprises flowing (e.g., pumping) liquid chlorine dioxide treatment solution through one or more baffles or laminar flow nozzles to achieve laminar flow.

In some embodiments, a method disclosed herein comprises pumping the liquid chlorine dioxide treatment solution, e.g., at a rate disclosed herein.

In some embodiments, the rate is about 1.5 GPM to about 18 GPM per linear foot of width (about 6 to 68 L/min per 0.3 m of width) of the curtain. In some embodiments, the rate is about 1.5 GPM to about 13.3 GPM per linear foot of width (about 6 to 50 L/min per 0.3 m of width) of the curtain. In some embodiments, the rate is about 1.5 GPM to about 12 GPM per linear foot of width (about 6 to 45 L/min per 0.3 m of width) of the curtain. In some embodiments, the rate is about 3 GPM to about 12 GPM (about 11 L/min to about 45 L/min) per linear foot (or per 0.3 m) of width of the curtain.

In some embodiments, the rate is about 1.5 GPM to about 5 GPM per linear foot of width of the curtain (about 6 to about 19 L/min per 0.3 m of width of the curtain). In some embodiments, the rate is about 3 GPM to about 5 GPM per linear foot of width of the curtain (about 11 to about 19 L/min per 0.3 m of width of the curtain). In some embodiments, the pumping rate is about 3 GPM to about 10 GPM per linear foot of width of the curtain (about 11 L/min to about 38 L/min per 0.3 m of width of the curtain).

In some embodiments, the rate is about 1 to 40 L/min. In some embodiments, the rate is about 10 to 30 L/min. In some embodiments, the rate is about 10 to 20 L/min. In some embodiments, the rate is about 3 to 5 GPM or about 11 to 19 L/min.

In some embodiments, forming a curtain of a liquid chlorine dioxide treatment solution comprises pumping the treatment solution such that it flows at a rate disclosed herein before it flows through the exit.

In some embodiments, the rate is about 1.5 GPM to about 18 GPM per linear foot of width (about 6 to 68 L/min per 0.3 m of width) of the curtain. In some embodiments, the rate is about 1.5 GPM to about 13.3 GPM per linear foot of width (about 6 to 50 L/min per 0.3 m of width) of the curtain. In some embodiments, the rate is about 1.5 GPM to about 13.3 GPM per linear foot of width (about 6 to 50 L/min per 0.3 m of width) of the curtain. In some embodiments, the rate is about 1.5 GPM to about 12 GPM per linear foot of width (about 6 to 45 L/min per 0.3 m of width) of the curtain. In some embodiments, the rate is about 3 GPM to about 12 GPM (about 11 L/min to about 45 L/min) per linear foot (or per 0.3 m) of width of the curtain.

In some embodiments, the rate is about 1.5 GPM to about 5 GPM per linear foot of width of the curtain (about 6 to about 19 L/min per 0.3 m of width of the curtain). In some embodiments, the rate is about 3 GPM to about 5 GPM per linear foot of width of the curtain (about 11 to about 19 L/min per 0.3 m of width of the curtain). In some embodiments, the pumping rate is about 3 GPM to about 10 GPM per linear foot of width of the curtain (about 11 L/min to about 38 L/min per 0.3 m of width of the curtain).

In some embodiments, the rate is about 1 to 40 L/min. In some embodiments, the rate is about 10 to 20 L/min. In some embodiments, the rate is about 3 to 5 GPM or about 11 to 19 L/min.

In some embodiments, the curtain flows downward (e.g., falls) under gravity. In some embodiments, a method disclosed herein comprises forming a liquid chlorine dioxide treatment solution that flows downward under gravity from a liquid exit onto a target surface (e.g., a surface in need of decontamination).

In some embodiments, the liquid chlorine dioxide treatment solution accelerates due to gravity as it flows downward, e.g., from the liquid exit onto the target surface.

In some embodiments, the curtain flows (e.g., falls) onto a target surface (e.g., a food product) in need of decontamination.

In some embodiments, the curtain is a stable curtain.

In some embodiments, the curtain is not constructed or arranged to allow air to pass through. Typically, the curtain substantially blocks air, as opposed to allowing ambient air to pass through. As used herein, a curtain that substantially blocks air means a curtain that blocks at least 80% of ambient air flow that is perpendicular to the curtain. In some embodiments, the curtain blocks at least 80%, 90% or 95% of ambient air flow that is perpendicular to the curtain.

In some embodiments, the curtain flows such that it does not break up into a sheet of droplets.

In some embodiments, the flow of fluid in the curtain is predominantly laminar. In some embodiments, the curtain flows laminarly.

Typically, the curtain does not consist of a sheet of droplets.

In some embodiments, the curtain contains no visible turbulence prior to contacting the target. In some embodiments, the curtain flows such that it is accelerated downwards under gravity. In some embodiments, at least part (e.g., most or all) of the curtain flows downward (e.g., falls vertically) under gravity. In some embodiments, the curtain flows downward (e.g., falls vertically) for a distance of at least 1 cm, e.g., 1 cm to 20 cm, e.g., 1 cm to 10 cm.

In some embodiments, the curtain is in the form of a sheet (e.g., a curved or flat sheet) that flows under gravity from a higher point to a lower point, e.g., a point where the curtain contacts a target surface. In some embodiments, the curtain is in the form of a flat sheet.

In some embodiments, the curtain (e.g., the stable curtain) has a depth of less than 1 inch (2.54 cm). In some embodiments, the curtain (e.g. the stable curtain) has a depth of 0.1 cm to 2.5 cm. In some embodiments, the curtain (e.g., the stable curtain) has a depth of less than 1 cm. In some embodiments, the curtain (e.g., the stable curtain) has a depth of less than 0.5 cm. In some embodiments, the curtain (e.g., the stable curtain) has a depth of less than 0.2 cm.

In some embodiments, the curtain (e.g., the stable curtain) has a depth in the range of about 0.05 cm to about 1 cm, about 0.05 cm to about 0.5 cm, or about 0.05 cm to about 0.2 cm.

In some embodiments, the curtain (e.g., the stable curtain) has a depth in the range of 0.05 cm to 1 cm, 0.05 cm to 0.5 cm, or 0.05 cm to 0.2 cm.

In some embodiments, the curtain (e.g., the stable curtain) has a depth in the range of 0.1 cm to 0.8 cm. In some embodiments, the curtain (e.g., the stable curtain) has a depth in the range of 0.1 cm to 0.5 cm.

In some embodiments, the curtain is free flowing (surrounded by free air or gas, as opposed to flowing along a solid surface) for at least a portion of (e.g., most of) its length. In some embodiments, the lower segment of the curtain is free flowing. In some embodiments, the free flowing curtain (e.g., the free flowing portion of the curtain) has a depth of less than 2.54 cm or less than 1 cm. In some embodiments, the free flowing curtain has a depth of about 0.05 cm to about 1 cm, about 0.05 cm to about 0.5 cm, or about 0.05 cm to about 0.2 cm.

In some embodiments, the free flowing curtain has a depth of 0.05 cm to 1 cm, 0.05 cm to 0.5 cm, or 0.05 cm to 0.2 cm.

In some embodiments, the curtain is free flowing at least immediately above (superior to) where it contacts a target surface. In some embodiments, the curtain is free flowing for a distance of at least 1 cm. In such embodiments, the curtain is free flowing for a distance of 1 cm to 30 cm, 1 cm to 20 cm, or 1 cm to 10 cm.

In some embodiments, the curtain flows along a solid surface (for at least part of, e.g., most of its length or all of its length). In some embodiments, at least part of one surface of the curtain flows over a solid surface that is oriented vertically or at a downwardly sloping angle such that the liquid that forms the curtain flows downwardly over the surface. In some such embodiments, the curtain flows downwardly over the solid surface and then falls onto a target surface.

Target Surface

Generally, the target surface is a surface (e.g., a surface of an object) in need of treatment with chlorine dioxide. In some embodiments, the target surface is a surface in need of decontamination. The decontamination can be for the purpose of killing or inactivating biological contaminants, such as, e.g., bacteria, viruses, fungi, or other biological contaminants that are killed or inactivated by chlorine dioxide. In some embodiments, a method disclosed herein reduces (e.g., kills or inactivates) a contaminant on a target surface. In some embodiments, the method provides at least a 1-log, 2-log, 3-log, 4-log, 5-log, or 6-log reduction in the contaminant.

The decontamination can also be for the purpose of oxidizing and/or breaking down a chemical contaminant. In some embodiments, a method disclosed herein oxidizes or breaks down at least 80%, 90%, or 95% of the chemical contaminant (these are w/w percentages).

In some embodiments, the target surface is an industrial surface that is contaminated by a chemical contaminant (e.g., a metal surface contaminated by a phenol).

In some embodiments, the target surface is a surface in need of bleaching.

In some embodiments, the target surface is a food product. The food product can be, e.g., a fruit, vegetable, meat, fish, shellfish, or egg. In some embodiments, the target surface is an egg.

In some embodiments, the target surface is a surface in a food processing facility (e.g., a food contact surface). In some embodiments, the target surface is a conveyor belt or other apparatus for moving a good (such as, e.g., a food product). In some embodiments, the target surface is a product (e.g., a food product) placed on a conveyor belt or other apparatus for moving goods.

In some embodiments, the target surface is a medical product (e.g., a veterinary product), such as a medical or veterinary instrument or device, in need of decontamination.

In some embodiments, the target surface is a metal surface in need of decontamination.

Contacting and Decontaminating

In some embodiments, a method disclosed herein comprises contacting a target surface (e.g., a surface in need of decontamination) with a curtain as described herein. In some embodiments, the contacting comprises moving (e.g., continuously or repeatedly moving) a target surface (e.g., a plurality of target surfaces) under or through the curtain such that the chlorine dioxide treatment solution contacts the target surface (e.g., the surface of a target object). In some embodiments, the target surface is a conveyor belt or other apparatus for moving goods (e.g., for continuously moving goods). In some embodiments, the target surface is an item (e.g., an item in need of decontamination, e.g. a food product) placed on a conveyor belt or other apparatus for moving goods.

In some embodiments, a method disclosed herein comprises repeatedly contacting a target surface (e.g., the surface of an object) with a curtain as disclosed herein. In one such embodiment, the method comprises moving a target object (such as, e.g., a food product or other target object, e.g., an object in need of decontamination) under or through such curtain multiple times to allow the chlorine dioxide treatment solution to contact the surface of the target object. In another such embodiment, the method comprises moving a target object (such as, e.g., a food product or other target object) under or through or through a plurality of such curtains. Moving a target object can be done using, e.g., a conveyor belt or similar apparatus.

In some embodiments a method disclosed herein comprises repeatedly contacting a target surface (e.g., the surface of an object) with a curtain (e.g., with a single curtain or a plurality of separate curtains) as disclosed herein so as to keep the target surface wetted with the chlorine dioxide treatment solution for a contact time of at least 1, 2, 3, 4, 5, 6, 7, 8, 9, 10, 12, 15, or 20 minutes (e.g., for a contact time that is in any range between 1 and 30 minutes, e.g., 1 to 20 minutes, 5 to 20 minutes, 1 to 10 minutes, 5 to 10 minutes, etc.).

In some embodiments wherein the target surface (e.g., the surface of an object) is repeatedly contacted with a curtain (e.g., with a single curtain or a plurality of separate curtains) as disclosed herein, the contacts can occur at regular or irregular intervals (e.g., at intervals ranging from 30 seconds to 20 minutes 1 minutes to 10 minutes, or 2 minutes to 5 minutes.

In some embodiments, a method disclosed herein decontaminates a target in need of decontamination. In some embodiments, a method disclosed herein reduces (e.g., kills or inactivates) a contaminant on a target surface. In some embodiments, the method provides at least a 1-log, 2-log, 3-log, 4-log, 5-log, or 6-log reduction in the contaminant.

In some embodiments a method disclosed herein comprises repeatedly contacting a target surface (e.g., the surface of an object) with a curtain as disclosed herein so as to so as to keep the target surface wetted with the chlorine dioxide treatment solution for a contact time sufficient to reduce (e.g., kill or inactivate) the level of a contaminant on the surface of the object (e.g., to provide at least a 1-log, 2-log, 3-log, 4-log, 5-log, or 6-log reduction in the contaminant).

Liquid Chlorine Dioxide Treatment Solution

The liquid chlorine dioxide treatment solution comprises chlorine dioxide and a liquid. The liquid can be, e.g., water, or another liquid carrier.

In some embodiments, the liquid chlorine dioxide treatment solution contains at least 0.5 ppm, 1 ppm, 2 ppm, or 3 ppm chlorine dioxide. In some embodiments, the liquid chlorine dioxide treatment solution contains up to 5 ppm, 10 ppm, 20 ppm, 50 ppm, 100 ppm, 500 ppm, 1000 ppm, 3000 ppm, 5000 ppm, or 6,000 ppm chlorine dioxide. In some embodiments, the liquid chlorine dioxide treatment solution comprises 0.5 to 5 ppm, 0.5 to 10 ppm, 1 ppm to 5 ppm, 1 ppm to 10 ppm, 2 ppm to 50 ppm, 2 ppm to 100 ppm, 2 ppm to 500 ppm, 2 ppm to 1000 ppm, 2 ppm to 3000 ppm, or 2 ppm to 5,000 ppm, or 2 ppm to 6,000 ppm chlorine dioxide.

In some embodiments, the liquid chlorine dioxide treatment solution comprises 1 ppm to 6,000 ppm chlorine dioxide.

In some embodiments, the liquid chlorine dioxide treatment solution comprises 1 ppm to 3,000 ppm to chlorine dioxide.

In some embodiments, the liquid chlorine dioxide treatment solution comprises 2 ppm to 3,000 ppm to chlorine dioxide.

In some embodiments, the liquid chlorine dioxide treatment solution comprises 3 ppm to 3,000 ppm to chlorine dioxide.

In some embodiments, the liquid chlorine dioxide treatment solution comprises 5 ppm to 3,000 ppm to chlorine dioxide.

In some embodiments, the liquid chlorine dioxide treatment solution is aqueous. In some embodiments, the liquid chlorine dioxide treatment solution consists essentially of water and chlorine dioxide. In some embodiments, the liquid chlorine dioxide treatment solution further comprises salt (e.g., NaCl). In some embodiments, the liquid chlorine dioxide treatment solution further comprises chlorite (e.g., sodium chlorite). In some embodiments, the liquid chlorine dioxide treatment solution further comprises salt (e.g., NaCl) and chlorite (e.g., sodium chlorite).

In some embodiments, the liquid chlorine dioxide treatment solution (e.g., the aqueous liquid chlorine dioxide treatment solution) comprises chlorine dioxide and a chlorine scavenging means (e.g., chlorite, e.g., sodium chlorite) for converting dissolved chlorine to chlorine dioxide. In some embodiments, the chlorine scavenging means comprises or consists of chlorite. In some embodiments, the chlorine scavenging means comprises or consists of sodium chlorite. In some embodiments, the chlorine scavenging means is sodium chlorite. In some embodiments, the liquid chlorine dioxide treatment solution comprises a ratio of chlorine scavenging means:chlorine dioxide in the range of about 1:4 to 1:15 (w/w) (e.g., about 1:10 to 1:15, e.g., about 1:13). In some embodiments, the chlorine scavenging means comprises sodium chlorite. In some embodiments, the chlorine scavenging means is sodium chlorite.

A liquid chlorine dioxide treatment solution to be used in the methods described herein can be prepared using methods known in the art. A liquid chlorine dioxide treatment solution of a desired concentration can be prepared by introducing a concentrated liquid solution of chlorine dioxide into a dilution fluid, e.g, dilution water. As used herein, the "concentrated liquid solution of chlorine dioxide" refers generally to a solution that has a higher concentration than the liquid chlorine dioxide treatment solution to be employed. In some embodiments, a method disclosed herein comprises making the liquid chlorine dioxide treatment solution by introducing a concentrated liquid solution of chlorine dioxide into dilution water. In some embodiments, the liquid chlorine dioxide treatment solution (or a concentrated liquid chlorine dioxide solution from which the chlorine dioxide treatment solution is prepared) is a solution as described in U.S. Pat. No. 7,678,388. In some embodiments, liquid chlorine dioxide treatment solution (or a concentrated liquid chlorine dioxide solution from which the chlorine dioxide treatment solution is prepared) is generated using a chlorine dioxide generator (e.g., a generator as disclosed in U.S. Pat. Nos. 6,486,479 and/or 6,645,457). Other methods known in the art can also be used to generate chlorine dioxide.

In some embodiments, the systems and methods disclosed herein involve recirculation of the liquid chlorine dioxide treatment solution. Recirculation allows the liquid chlorine dioxide treatment solution to be re-used. During recirculation the chlorine dioxide concentration of the liquid treatment solution is expected to diminish (in part due to the demand of surfaces contacted by the treatment solution) unless chlorine dioxide is added. Accordingly, chlorine dioxide, or a concentrated liquid solution of chlorine dioxide, can be added to the liquid chlorine dioxide treatment solution while it is being circulated so as to maintain its concentration and thus its efficacy in treating surfaces as disclosed herein. Thus, the liquid chlorine dioxide treatment solution itself, which is circulating through a delivery system, can also serve as a dilution fluid to which chlorine dioxide is added. Chlorine dioxide can be added with a chlorine dioxide generator (e.g., by using a stream of the treatment solution as the drive fluid for a venturi in a chlorine dioxide generator, e.g., as disclosed in U.S. Pat. Nos. 6,486,479 and/or 6,645,457) or by adding an appropriate amount of a concentrated liquid chlorine dioxide solution.

In some embodiments, the liquid chlorine dioxide treatment solution (or a concentrated liquid chlorine dioxide solution from which the chlorine dioxide treatment solution is prepared) is an aqueous solution that comprises a chlorine dioxide concentration of 200 to 10,000 mg/L (e.g., 500 to 10,000 mg/L) and has a pH of 1 to 8 (e.g., about 5 to 8, e.g., about 6 to 8).

In some embodiments, the liquid chlorine dioxide treatment solution (or a concentrated liquid chlorine dioxide solution from which the chlorine dioxide treatment solution is prepared) is an aqueous solution comprising 500-3500 ppm chlorine dioxide and 100 to 1000 ppm chlorite.

In some embodiments, the liquid chlorine dioxide treatment solution (or a concentrated liquid chlorine dioxide solution from which the chlorine dioxide treatment solution is prepared) has a pH of 1 to 6 (e.g., 4 to 6, e.g., 5 to 6). In some embodiments, the liquid chlorine dioxide treatment solution (or a concentrated liquid chlorine dioxide solution from which the chlorine dioxide treatment solution is prepared) is prepared to include a chlorine scavenging means (e.g., chlorite, e.g., sodium chlorite). In some embodiments, the liquid chlorine dioxide treatment solution (or a concentrated liquid chlorine dioxide solution from which the chlorine dioxide treatment solution is prepared) comprises sodium chlorite, wherein the solution is prepared such that the ratio of sodium chlorite:chlorine dioxide is initially in the range of about 1:4 to 1:15 (w/w) (e.g., about 1:10 to 1:15, e.g., about 1:13).

In some embodiments, the concentrated liquid chlorine dioxide solution and/or the liquid chlorine dioxide treatment solution comprises at least 90% by weight of chlorine dioxide with respect to all chlorine species. In some embodiments, the concentrated liquid solution of chlorine dioxide and/or the liquid chlorine dioxide treatment solution comprises at least 95% by weight of chlorine dioxide with respect to all chlorine species.

In some embodiments, the liquid chlorine dioxide treatment solution is not made from electrolytically generated chlorine dioxide.

In some embodiments, the liquid chlorine dioxide treatment solution is not made from activated chlorine dioxide. "Activated chlorine dioxide" as used herein refers to chlorine dioxide created by directly mixing chlorite (e.g., sodium chlorite or sodium chlorite solution) with an acid or acid solution).

In some embodiments, the liquid chlorine dioxide treatment solution (and/or a concentrated liquid chlorine dioxide solution from which it is made) contains at least 90%, 95%, 98% or 99% by weight chlorine dioxide relative to chlorine ($Cl_2$). In some embodiments, the liquid chlorine dioxide treatment solution (and/or a concentrated liquid chlorine dioxide solution from which it is made) contains no detectable chlorine ($Cl_2$).

The concentration of chlorine dioxide and other chlorine species can be determined using known methods. For example, the concentration of chlorine dioxide in a solution can also be determined using a commercially available testing device, e.g., a Palintest ChlordioX Plus device. In preferred embodiments, the concentration is determined by Method 4500-C102E ("Amperometric Method II") in the "Standard Methods for the Examination of Water and Wastewater," 20th ed., 1998, or an equivalent method.

Temperature

In some embodiments, a method disclosed herein comprises maintaining the liquid chlorine dioxide treatment solution at a particular temperature. In some embodiments, the method comprises maintaining the liquid chlorine dioxide treatment solution at a temperature of at least 90° F. (32.2° C.). In some embodiments, the method comprises maintaining the liquid chlorine dioxide treatment solution at a temperature of at least 100° F. (37.8° C.), 105° F. (40.6° C.), 110° F. (43.3° C.) or 115° F. (46.1° C.). In some embodiments, the method comprises maintaining the liquid chlorine dioxide treatment solution at a temperature of up to 120° F. (48.9° C.), 130° F. (54.4° C.), 140° F. (60° C.), 150° F. (65.6° C.), 160° F. (71.1° C.), 170° F. (76.6° C.) or 180° F. (82.2° C.). In some embodiments, the method comprises maintaining the liquid chlorine dioxide treatment solution at a temperature of 100° F. to 180° F. (37.8° C. to 82.2° C.). In some embodiments, the method comprises maintaining the liquid chlorine dioxide treatment solution at a temperature of 100° F. to 150° F. (37.8° C. to 65.6° C.). In some embodiments, the method comprises maintaining the liquid chlorine dioxide treatment solution at a temperature of 90° F. to 120° F. (32.2° C. to 48.9° C.).

In some embodiments, the method comprises maintaining the liquid chlorine dioxide treatment solution at a temperature of 100° F. to 120° F. (37.8° C. to 48.9° C.). In some embodiments, the method comprises maintaining the liquid chlorine dioxide treatment solution at a temperature of 110° F. to 120° F. (43.3° C. to 48.9° C.). In some embodiments, the method is performed at an ambient temperature of up to 100° F. (37.8° C.). In some embodiments, the method is performed at an ambient temperature of 50° F. (10° C.) to 90° F. (32.2° C.). In some embodiments, the method is performed at an ambient temperature of 60° F. (15° C.) to 80° F. (26.7° C.).

In some embodiments, the method is performed at an ambient temperature disclosed herein and comprises maintaining the liquid chlorine dioxide solution and at a temperature disclosed herein, or within a temperature range disclosed herein.

In some embodiments, the liquid chlorine dioxide treatment solution is at least 20° F. (11.1° C.) warmer than the ambient temperature. In some embodiments, the temperature difference between the ambient temperature and the liquid chlorine dioxide treatment solution is at least 30° F. (16.7° C.), 40° F. (22.2° C.), or 50° F. (27.8° C.) (i.e., the liquid chlorine dioxide treatment solution is at least 30° F. (16.7° C.), 40° F. (22.2° C.), or 50° F. (27.8° C.) warmer than the ambient temperature).

In some embodiments, the method comprises maintaining the liquid chlorine dioxide treatment solution at a temperature that is at least 20° F. (11.1° C.), 30° F. (16.7° C.), 40° F. (22.2° C.), or 50° F. (27.8° C.) higher than the ambient temperature.

Systems

Also provided herein are systems for treating a target surface (e.g., a target surface in need of decontamination) with chlorine dioxide. The systems can be used to carry out certain methods disclosed herein.

One embodiment of such a system is disclosed in FIG. 2A.

The system includes a liquid chlorine dioxide treatment solution 105 and a pump 100 for pumping liquid chlorine dioxide treatment solution (e.g., a solution as disclosed herein, e.g., a solution containing at least 5 ppm chlorine dioxide) to form a flowing treatment solution. In some embodiments, the pump pumps, or is capable of pumping, the treatment solution at a rate disclosed herein.

The system also includes a (first) conduit 110 through which flowing treatment solution flows to a liquid exit 130. The conduit can be, or can include, an open channel such as a trough, through which treatment solution flows.

Additionally, the system includes a means 120 for removing turbulence and/or for creating laminar flow in flowing solution. Such means can be, e.g., one or more baffles or laminar flow nozzles. Examples of baffles are shown in FIG. 4A (left side) and FIG. 4B (right side showing X baffle system). Baffle systems for removing turbulence and/or creating laminar flow are commercially available and are marketed for creating waterfalls for decorative purposes. A system disclosed herein can also include parallel surfaces (such as those shown on the right side of FIG. 4A and the left side of FIG. 4B) through which water flows before it drops to form a curtain.

The system further includes a liquid exit 130, from which flowing treatment solution flows (e.g., falls) downward under gravity to form a curtain. Typically, a collecting container or conduit 150 is located beneath the liquid exit so as to collect treatment solution after it has flowed through the curtain. In some embodiments, the exit is the edge of a trough from which treatment solution falls. Some non-limiting examples of liquid exits are shown in FIG. 3A to FIG. 3D.

In some embodiments, the collecting container or conduit is located not more than 0.5 m or not more than 0.3 m beneath the liquid exit.

Figure 2B:
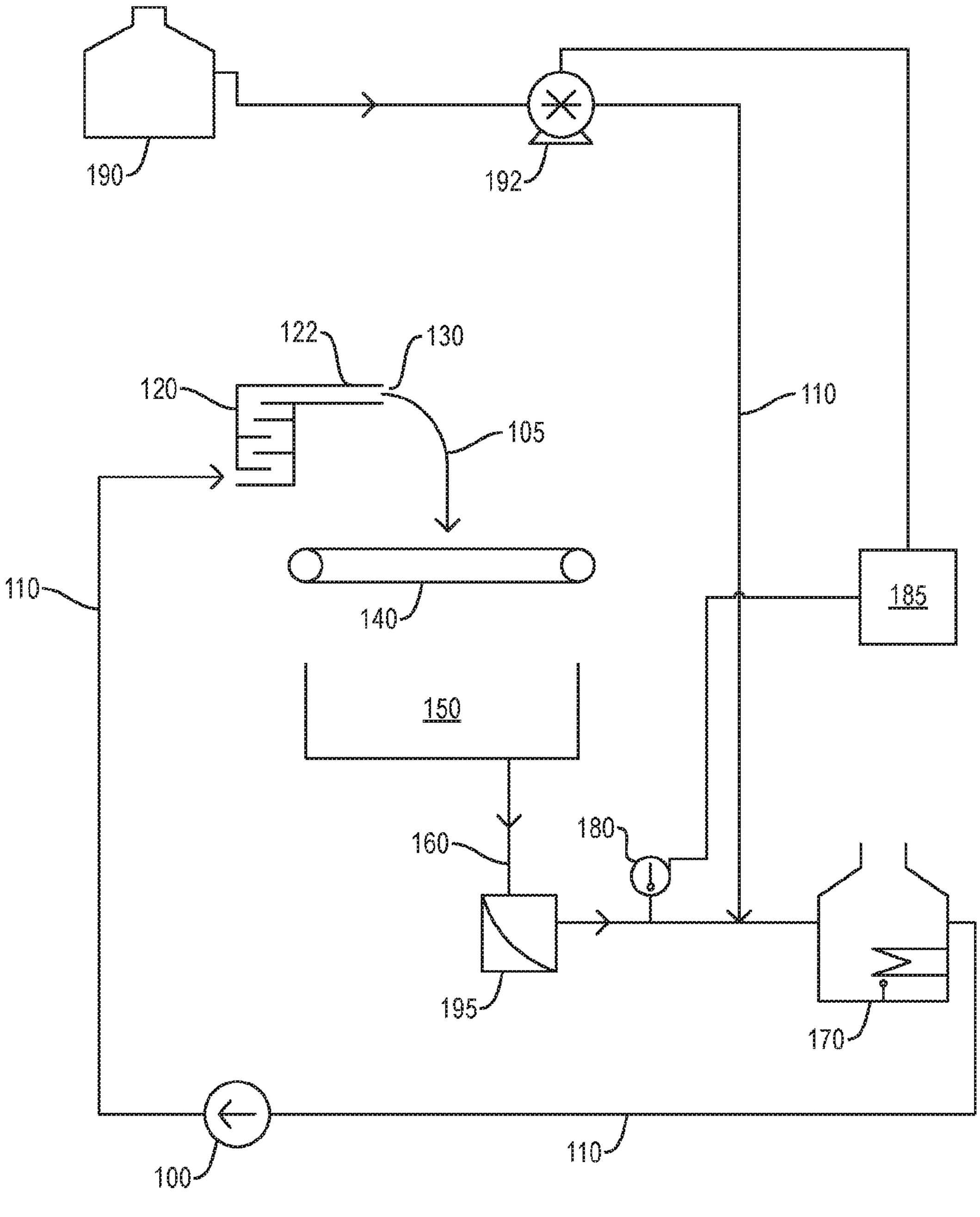
FIG. 2B depicts components of an embodiment of a system disclosed herein.

The systems disclosed herein can optionally include other components such as those disclosed in FIG. 2B.

The system in FIG. 2B includes a pump 100 for pumping liquid chlorine dioxide treatment solution through a (first) conduit 110.

In some embodiments, the system includes liquid chlorine dioxide treatment solution 105, e.g., a liquid chlorine dioxide treatment solution as disclosed herein.

Figure 3A:
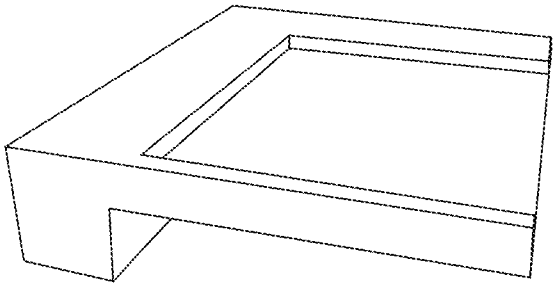
FIG. 3A to FIG. 3D depict examples of liquid exits that can be used to form a curtain as described herein.
Figure 3B:
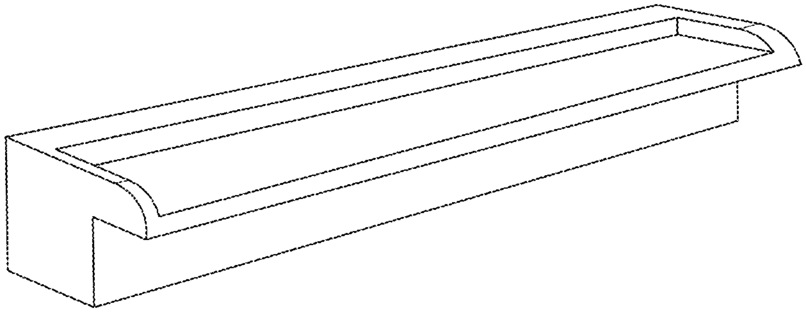
Figure 3C:
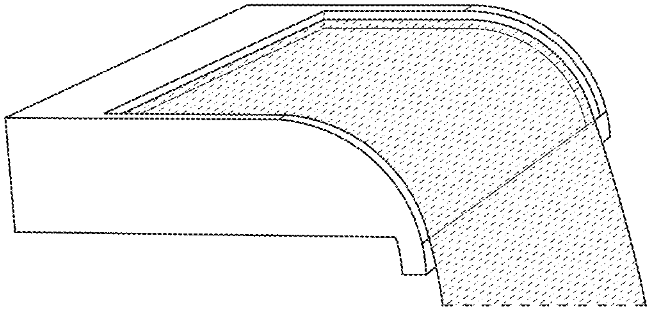
Figure 3D:
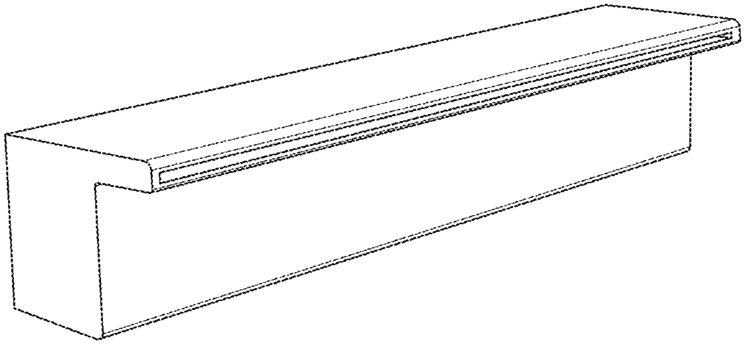

Typically, the system includes a means 120 for removing turbulence and/or for creating laminar flow in flowing solution, e.g., a means comprising baffles and/or laminar flow nozzles. The means 120 for removing turbulence and/or for creating laminar flow can also include parallel surfaces 122 (which can be connected by sides, e.g., as shown in FIG. 3D) through which the treatment solution flows before it drops from a liquid exit 130 to form a curtain. In some embodiments, the liquid exit is an elongated opening between two parallel surfaces from which the treatment solution falls to form a free flowing curtain.

In some embodiments, the system includes a target surface 140, e.g., a surface as disclosed herein. The surface can be, e.g., a target surface in need of decontamination. The surface is located under the curtain. In some embodiments, the surface moves through the curtain, e.g., the surface is a conveyor belt or an object on a conveyor belt as disclosed herein.

In some embodiments, the system is configured to produce a curtain having a height as disclosed herein. In embodiments wherein the system includes a target surface 140, as shown in FIG. 2B (and also in FIG. 5 and FIG. 6), the height of the curtain is measured as the vertical distance from the liquid exit to the surface. If the system does not include a target surface, the height of the curtain is measured as the shortest vertical distance from the liquid exit to a location where the curtain contacts the collecting conduit or container 150. In some embodiments, the system is configured to produce a curtain with a height 2 inches to 20 inches (5 cm to 51 cm) (e.g., 0.1 m to 0.5 m, 0.1 m to 0.3 m) or a height of 1.5 ft (about 0.5 m) or less, 1 ft (about 0.3 m) or less, 11 inches (28 cm) or less, or 8 inches (20.3 cm) or less. In some embodiments, the system is configured to produce a curtain with a height of 1 in. to 12 in. (2.5 cm to 30.5 cm) or 2 in to 10 in. (5 cm to 25.5 cm).

In some embodiments, the system includes a means for maintaining the treatment solution at a desired temperature 170, e.g., a temperature disclosed herein. In some embodiments, the means is a heating or cooling device. In some embodiments, the means is a device (e.g., a water heater) suitable for keeping the treatment solution warmer than the ambient temperature, e.g., heating the treatment solution to a temperature disclosed herein. In some embodiments, the temperature is a temperature of at least 100° F. (37.8° C.), 105° F. (40.6° C.), 110° F. (43.3° C.) or 115° F. (46.1° C.). In some embodiments, the temperature is a temperature of 100° F. (37.8° C.) to 120° F. (48.9° C.), e.g. 110° F. (43.3° C.) to 120° F. (48.9° C.). In some embodiments, the temperature is at least 20° F. (11.1° C.), 30° F. (16.7° C.), 40° F. (22.2° C.), or 50° F. (27.8° C.) warmer than the ambient temperature. In one embodiment, the heating device comprises a tank with a heating element, as is depicted in FIG. 2B. Alternatively, or in addition, the heating device can comprise heating elements (e.g., coils) that wrap around, or are within, a fluid conduit such as conduit 110 or any conduit in fluid connection with conduit 110.

In some embodiments, the system includes an assessment meter 180 for assessing chlorine dioxide concentration in the solution. The meter can directly or indirectly measure chlorine dioxide concentration. Such assessment meters are commercially available and include the Palintest ChlordioX Plus device, the Optek AF26 VIS/NIR sensor for inline chlorine dioxide monitoring, and ORP meters (which allow indirect assessment of chlorine dioxide concentration by measuring oxidation reduction potential).

In some embodiments, the system includes a connecting conduit 160 for recirculating treatment solution. The connecting conduit allows treatment solution to be circulated back through the curtain. Generally, the connecting conduit funnels treatment solution collected in the collecting container or conduit such that it flows back through the first conduit (and said means for removing turbulence) and the liquid exit. The collecting conduit and the connecting conduit can be a single conduit in fluid connection with the first conduit. In some embodiments, the collecting conduit, the connecting conduit, and the first conduit are parts of one connected fluid conduit.

In some embodiments, the system includes chlorine dioxide introduction apparatus for adding chlorine dioxide to the treatment solution, e.g., so as to achieve a chlorine dioxide concentration or concentration range disclosed herein. The chlorine dioxide introduction apparatus typically includes a source of chlorine dioxide 190, such as a generator that generates chlorine dioxide, a concentrated liquid chlorine dioxide solution, or a container that holds a concentrated liquid chlorine dioxide solution). Such chlorine dioxide introduction apparatus can also include a conduit and/or pump 192, which can be connected with an analyzer 185 that receives input from meter 180 and controls the introduction of chlorine dioxide into the treatment solution.

In some embodiments, the system includes an analyzer (adjusting means) 185 for adjusting a dose of chlorine dioxide that is added to the treatment solution. In such embodiments, the system is typically a recirculating system. The analyzer can be any device that transfers information about a measured concentration of chlorine dioxide in the solution (e.g., a concentration measured using the assessment meter) to the chlorine dioxide introduction apparatus, such that the amount of chlorine dioxide added by such apparatus is adjusted, if needed, so as to maintain a desired chlorine dioxide concentration in the treatment solution (e.g., a concentration or concentration range as disclosed herein). For example, the analyzer can be a computer or other device that receives input from the assessment meter regarding an assessed concentration of chlorine dioxide and causes the chlorine dioxide introduction apparatus to adjust the amount of chlorine dioxide added, if needed, so as to maintain a desired chlorine dioxide concentration in the treatment solution (e.g., a concentration or concentration range as disclosed herein).

In some embodiments, the system includes a filter 195. The filter can be, e.g., a parabolic filter.

Figure 5:
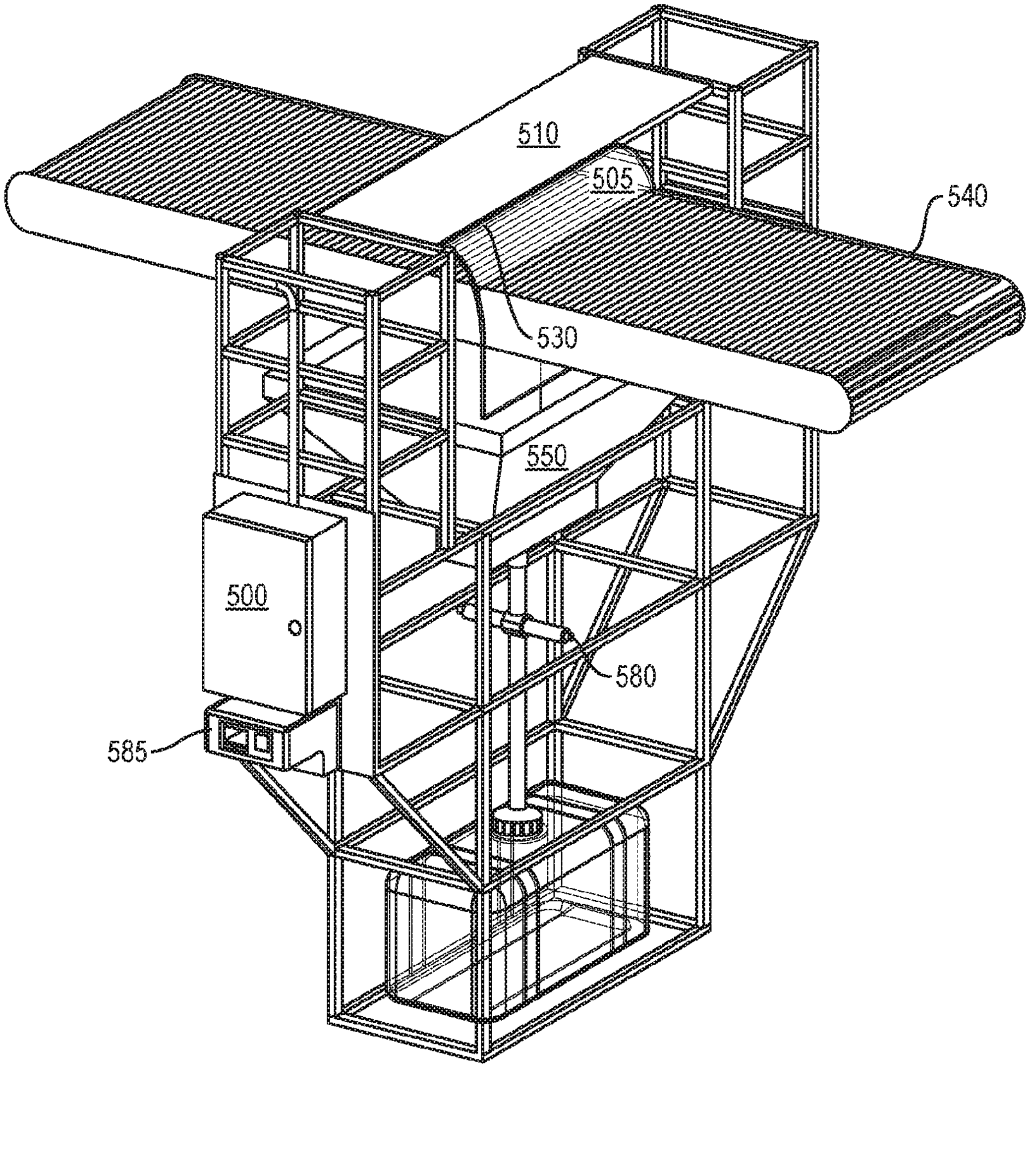
FIG. 5 shows another embodiment of a system disclosed herein.

FIG. 5 shows an embodiment of a system used for creating a curtain of liquid chlorine dioxide treatment solution 505. The system includes a pump 500 and conduit 510. The conduit generally includes internal baffles (not shown in FIG. 5; see, e.g., FIG. 4A and FIG. 4B), and the liquid chlorine dioxide flows out of a liquid exit 530 to form a curtain (e.g., 502). In the depicted embodiment, the system includes a conveyor belt 540 that moves beneath the liquid exit to move objects in need of decontamination through the curtain. The system also includes a collecting conduit or container 550. In some embodiments, the system includes a meter 580 and optionally an analyzer 585. The analyzer can be used to control the formation of incoming liquid chlorine dioxide treatment solution from a chlorine dioxide source (e.g., a concentrated liquid chlorine dioxide solution) and a dilution fluid (typically water).

Figure 6:
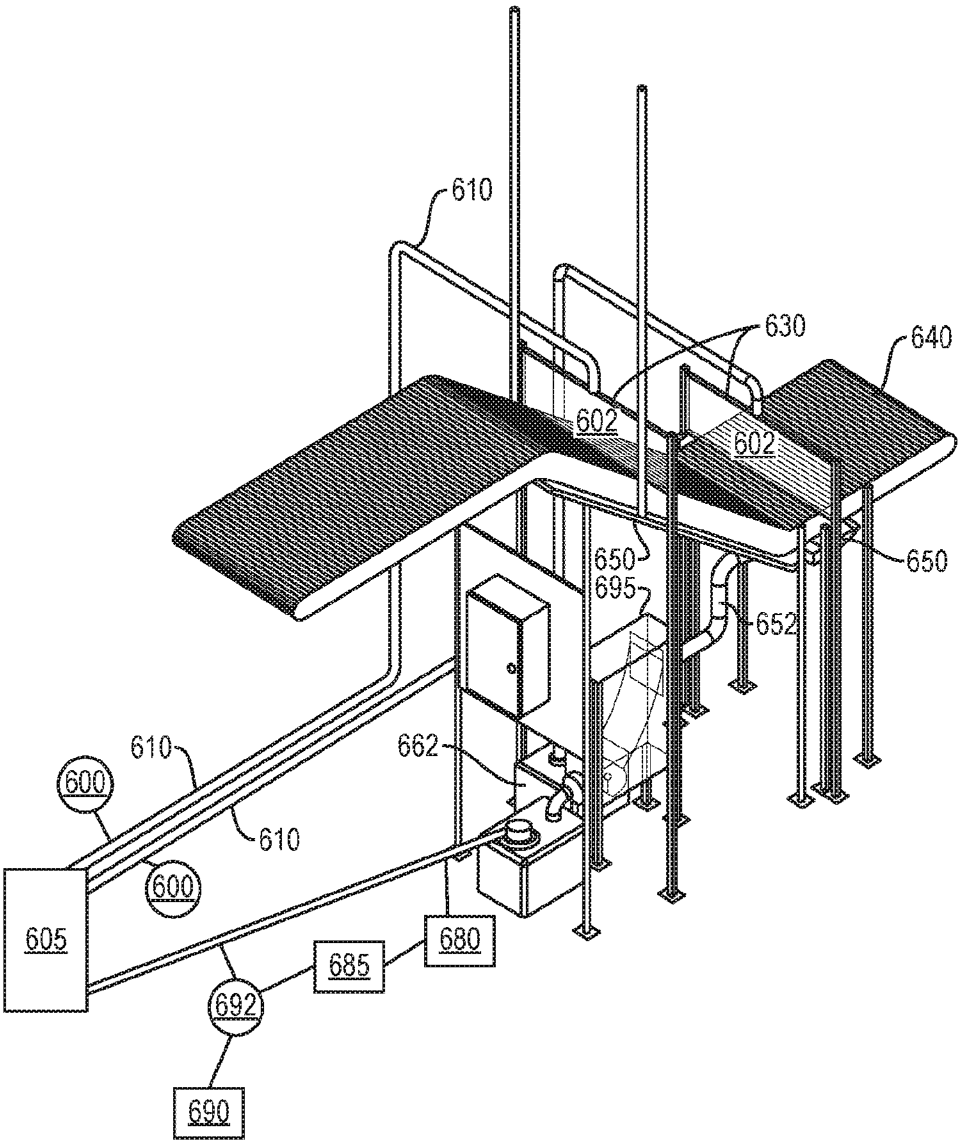
FIG. 6 shows another embodiment of a system disclosed herein.

FIG. 6 shows another embodiment of a system. The systems disclosed herein can be configured to produce a plurality of curtains (e.g., two curtains as illustrated in FIG. 5) and/or to utilize recirculation, as is depicted in FIG. 6. The systems disclosed herein can include a plurality of components (such as, e.g., pumps, conduits, liquid exits, and means for removing turbulence) to form a plurality of curtains. The system can include a liquid chlorine dioxide treatment solution 605 and/or a tank or other container for holding such a treatment solution. The system includes a conduit 610 and a pump 600 for pumping liquid chlorine dioxide treatment solution to a liquid exit 630 through which treatment solution flows (e.g., falls) to form the curtain. As in the embodiment shown in FIG. 6, the liquid exit can be a slit in a pipe. Typically, the slit is a smooth slit configured to form a curtain as disclosed herein (e.g., a curtain that is stable and/or has laminar flow). For example, the slit can be a laser cut slit in a PVC pipe.

The system can include a target surface beneath the liquid exit. In some embodiments, the target surface is a conveyor belt (e.g., 640 or 540) that can be used to carry objects in need of treatment with chlorine dioxide (e.g., objects in need of decontamination) through the curtain or curtains. Examples of systems including conveyor belts are shown in FIG. 5 and FIG. 6.

The system can also include a collecting conduit or container beneath the liquid exit (e.g., plurality of liquid exits). As shown in FIG. 6, a collecting conduit or container (e.g., conduit or container 650) can be elongated and/or sloped, which can allow collection of treatment solution that flows through more than one curtain. Alternatively, multiple collecting conduits or containers can be used to collect fluid from multiple curtains.

In some embodiments, the system further includes a filter (e.g., a parabolic filter, e.g., filter 695) through which collected fluid from the collecting conduit or container 650 flows. The collecting conduit or container can be connected with the filter via a further conduit 652. In some embodiments, the system includes a container 662 for collecting solids filtered out by the filter.

The solution that is collected, and optionally filtered, can be disposed of, or it can be re-used to form additional treatment solution by adding chlorine dioxide using a chlorine dioxide introduction system. The chlorine dioxide introduction system can include a meter 680 for assessing chlorine dioxide concentration, an analyzer 685 for adjusting a dose of chlorine dioxide to be added based on the assessed concentration, and a chlorine dioxide introduction apparatus, which generally includes a source of chlorine dioxide (e.g., 690, which can be, e.g., a chlorine dioxide generator or a concentrated liquid solution of chlorine dioxide) and optionally a pump 692 for pumping chlorine dioxide (which is typically in the form of a concentrated liquid chlorine dioxide solution) that is introduced into collected solution that recirculates through the system.

Certain systems disclosed herein can be used to carry out methods disclosed herein. Accordingly, relevant features or elements of methods disclosed herein can also be included in systems disclosed herein. For instance, in some embodiments the system is configured to produce a curtain that has features (e.g., a height and/or depth) as disclosed herein.

Typically, the systems and methods disclosed herein do not include a swimming pool or spa. Generally, the systems and methods disclosed herein are not for use for decorative purposes and are for, or primarily for, utilitarian purposes as disclosed herein (e.g., for decontamination of surfaces). In some embodiments, the systems disclosed herein are for use within a food processing plant.

In some embodiments, the systems disclosed herein do not include components or features not disclosed herein. In some embodiments, the systems disclosed herein do not include a swimming pool. In some embodiments, the systems disclosed herein do not include a filter. In some embodiments, the systems disclosed herein do not include a swimming pool filter. In some embodiments, the systems disclosed herein do not include an electrolytic device.

Aspects and Embodiments

In one aspect provided herein is a method of applying a liquid chlorine dioxide treatment solution, the method comprising forming a stable curtain of a liquid chlorine dioxide treatment solution that flows downward under gravity from a liquid exit onto a target surface in need of decontamination.

In some embodiments, forming the stable curtain comprises flowing the liquid chlorine dioxide solution through one or more baffles or laminar flow nozzles to form a stream of liquid chlorine dioxide solution with laminar flow that flows from the liquid exit. In some embodiments, forming the stable curtain comprises flowing the liquid chlorine dioxide solution through one or more baffles to form a laminar flow stream.

In some embodiments, treatment solution at the location where the curtain contacts the target surface retains at least 70%, 75%, 80%, 85% or 90% of a chlorine dioxide concentration that is initially present in treatment solution before it passes through the liquid exit.

In some embodiments, the curtain has a height of 2 inches to 20 inches (5 cm to 51 cm). In some embodiments, the curtain has a height of about 1.5 ft (about 0.5 m) or less. In some embodiments, the curtain has a height of about 1 ft (about 0.3 m) or less. In some embodiments, the curtain has a height of 11 inches (28 cm) or less. In some embodiments, the curtain has a height of 8 inches (20.3 cm) or less. In some embodiments, the curtain has a height of 0.1 to 0.5 m. In some embodiments, the curtain has a height of 0.1 to 0.3 m. In some embodiments, the curtain has a height of 1 in. to 12 in. (2.5 cm to 30.5 cm) or 2 in to 10 in. (5 cm to 25.5 cm).

In some embodiments, the curtain has a depth disclosed herein, e.g., a depth of 0.05 cm to 1 cm.

In one embodiment, the method comprises maintaining the liquid chlorine dioxide treatment solution at a temperature of at least 100° F. (37.8° C.), 105° F. (40.6° C.), 110° F. (43.3° C.) or 115° F. (46.1° C.).

In some embodiments, a method disclosed herein comprises pumping liquid chlorine dioxide treatment solution so as to form a flowing stream before said stream exits through the liquid exit to form the curtain.

In some embodiments, the method comprises pumping the stream through one or more baffles or laminar flow nozzles to form a laminar flow stream which flows to the liquid exit. In some embodiments, the method comprises pumping the stream through one or more baffles to form a laminar flow stream that falls from the liquid exit to form the curtain.

In some embodiments, the curtain is transparent.

In some embodiments, the rate is about 1.5 GPM to about 18 GPM per linear foot of width (about 6 to 68 L/min per 0.3 m of width) of the curtain. In some embodiments, the pumping rate is about 1.5 GPM to about 12 GPM per linear foot of width (about 6 to 45 L/min per 0.3 m of width) of the curtain. In some embodiments, the rate is about 3 GPM to about 12 GPM (about 11 L/min to about 45 L/min) per linear foot (or per 0.3 m) of width of the curtain.

In some embodiments, the pumping rate is about 1.5 GPM to about 5 GPM per linear foot of width of the curtain (about 6 to about 19 L/min per 0.3 m of width of the curtain). In some embodiments, the rate is about 3 GPM to about 5 GPM per linear foot of width of the curtain (about 11 to about 19 L/min per 0.3 m of width of the curtain). In some embodiments, the pumping rate is about 3 GPM to about 10 GPM per linear foot of width of the curtain (about 11 L/min to about 38 L/min per 0.3 m of width of the curtain).

In some embodiments, the pumping is at a rate of about 1 L/min to 40 L/min. In some embodiments, the rate is about 10 L/min to 20 L/min. In some embodiments, the rate is about 3 GPM to 5 GPM or about 11 L/min to 19 L/min.

In another aspect provided herein is a method comprising (i) forming a curtain of a liquid chlorine dioxide treatment solution that flows downward under gravity, and (ii) contacting a target surface in need of decontamination with the curtain.

In some embodiments, the curtain is stable.

In some embodiments, the method comprises flowing (e.g., pumping) liquid chlorine dioxide treatment solution through one or more baffles or laminar flow nozzles to form a laminar flow stream that passes through a liquid exit to form the curtain.

In some embodiments, the flowing (e.g., pumping) is at a rate disclosed herein. In some embodiments, the rate is about 1.5 GPM to 12 GPM per linear foot of width of the curtain.

In some embodiments, the curtain has a height of 0.1 to 0.3 m.

In some embodiments, the curtain has a depth of 0.05 cm to 1 cm.

In some embodiments, the method comprises maintaining the liquid chlorine dioxide treatment solution at a temperature of at least 100° F. (37.8° C.), 105° F. (40.6° C.), 110° F. (43.3° C.) or 115° F. (46.1° C.). In some embodiments, the method comprises heating the liquid chlorine dioxide treatment solution to keep it at a temperature of 100° F. (37.8° C.) to 120° F. (48.9° C.), e.g. 110° F. (43.3° C.) to 120° F. (48.9° C.). In some embodiments, the liquid chlorine dioxide treatment solution is at least. 20° F. (11.1° C.), 30° F. (16.7° C.), 40° F. (22.2° C.), or 50° F. (27.8° C.) warmer than the ambient temperature.

In some embodiments, the ambient temperature is 50° F. (10° C.) to 90° F. (32.2° C.) or 60° F. (15° C.) to 80° F. (26.7° C.).

In some embodiments, the method further comprises pumping liquid chlorine dioxide treatment solution so as to form a flowing stream before said stream exits through a liquid exit to form the curtain.

In some embodiments, liquid chlorine dioxide treatment solution that contacts the target surface retains at least 70%, 75%, 80%, 85% or 90% of a chlorine dioxide concentration that is present in the treatment solution that flows through the liquid exit. The chlorine dioxide concentration of the treatment fluid at the relevant locations (e.g., where the curtain contacts the target and where the treatment solution flows through the liquid exit) can be assessed, for example, continuously or by assessing the concentration in one or more samples drawn from the applicable location.

In some embodiments, the pumping is at a rate of about 1 to 40 L/min. In some embodiments, the rate is about 10 to 20 L/min. In some embodiments, the rate is about 3 to 5 GPM or about 11 to 19 L/min.

In one embodiment, the method comprises maintaining the liquid chlorine dioxide treatment solution at a temperature of at least 100° F. (37.8° C.), 105° F. (40.6° C.), 110° F. (43.3° C.) or 115° F. (46.1° C.).

In some embodiments, the method comprises heating the liquid chlorine dioxide treatment solution to a temperature disclosed herein, e.g., a temperature of at least 100° F. (37.8° C.), 105° F. (40.6° C.), 110° F. (43.3° C.) or 115° F. (46.1° C.).

In some embodiments, the method comprises maintaining the liquid chlorine dioxide treatment solution at a temperature that is at least 20° F. (11.1° C.), 30° F. (16.7° C.), 40° F. (22.2° C.), or 50° F. (27.8° C.) higher than the ambient temperature.

In some embodiments, contacting the target surface with the curtain comprises moving a target object under or through the curtain such that the liquid chlorine dioxide treatment solution runs over the target object.

In some embodiments, methods disclosed herein involve recirculation of liquid chlorine dioxide treatment solution through the curtain. In some embodiments, chlorine dioxide is added to recirculating chlorine dioxide treatment solution. The chlorine dioxide can be added in a fixed or variable dose. In some embodiments, the dose is variable and is selected (e.g., based on measurements of chlorine dioxide concentration in the solution after it contacts the target surface) so as to maintain a desired concentration (e.g., a concentration disclosed herein) of chlorine dioxide in the liquid chlorine dioxide treatment solution.

In another aspect provided herein is a method comprising (i) forming a curtain of a liquid chlorine dioxide treatment solution that flows downward under gravity from a liquid exit, (ii) contacting a target surface in need of decontamination with the curtain, (iii) collecting liquid treatment solution that has flowed downwards through the curtain to make collected solution, and (iv) recycling the collected solution by recirculating it through the liquid exit.

In some embodiments, the method further comprises introducing chlorine dioxide into the collected solution.

In some embodiments, the liquid chlorine dioxide treatment solution that contacts the target surface retains at least 70%, 75%, 80%, 85% or 90% of a chlorine dioxide concentration that is present in the treatment solution that flows through the liquid exit.

In some embodiments, the method further comprises measuring a residual concentration of chlorine dioxide in the collected solution. In some embodiments, the method comprises introducing a dose of chlorine dioxide into the collected solution, wherein the dose is effective to maintain a concentration of chlorine dioxide in the liquid chlorine dioxide treatment solution (e.g., to maintain the concentration at a concentration or within a target range, e.g., a concentration or concentration range disclosed herein).

In a further aspect provided herein is a method of forming a recirculating stable curtain of a liquid chlorine dioxide treatment solution to deliver chlorine dioxide to a target surface, the method comprising (i) forming a stable curtain of a liquid chlorine dioxide treatment solution that flows downward under gravity, (ii) contacting a target surface in need of decontamination with the curtain, (iii) collecting liquid treatment solution that has flowed downwards through the curtain to make collected solution, (iv) introducing chlorine dioxide into collected solution and (v) recycling collected solution into which chlorine dioxide has been introduced by using it to form the stable curtain.

In some embodiments, the method comprises pumping liquid chlorine dioxide treatment solution through one or more baffles or laminar flow nozzles to form stream that flows laminarly and passes through a liquid exit to form the curtain. In some embodiments, the method comprises pumping liquid chlorine dioxide treatment solution through one or more baffles.

In some embodiments, treatment solution at the location where the curtain contacts the target surface retains at least 70%, 75%, 80%, 85% or 90% of a chlorine dioxide concentration that is initially present in treatment solution at the location where it first forms the curtain. The chlorine dioxide concentration of the treatment fluid at each of the relevant locations (e.g., where the curtain contacts the target and where the curtain first forms) can be assessed, for example, continuously or by assessing the concentration in one or more samples drawn from the applicable location.

In one embodiment, the method comprises (i) forming a stable curtain of a liquid chlorine dioxide treatment solution that flows downward under gravity from a liquid exit, (ii) contacting a target surface in need of decontamination with the curtain, (iii) collecting liquid treatment solution that has flowed downwards through the curtain to make collected solution, (iv) introducing chlorine dioxide into collected solution and (v) recycling collected solution into which chlorine dioxide has been introduced by recirculating it through the liquid exit.

In some embodiments, the method further comprises measuring a residual concentration of chlorine dioxide in the collected solution.

In some embodiments, the chlorine dioxide that is introduced into the collected solution is introduced at a dose that is effective to maintain a concentration of chlorine dioxide in the liquid chlorine dioxide treatment solution that flows through the liquid exit.

In some embodiments, the method comprises measuring a residual concentration of chlorine dioxide in the collected solution and adjusting the dose that is introduced so as to maintain the concentration.

In some embodiments, the concentration maintained is at least 2 ppm.

In some embodiments, the concentration maintained is between 2 ppm and 50 ppm.

In some embodiments, the concentration maintained is between 2 ppm and 10 ppm.

In some embodiments, contacting the target surface in need of decontamination with the curtain comprises moving a target object under or through the curtain such that the liquid chlorine dioxide treatment solution runs over the target object.

In some embodiments, the treatment solution at a location where the curtain contacts the target surface retains at least 70%, 75%, 80%, 85% or 90% of the chlorine dioxide concentration that is initially present in the treatment solution that flows from of the liquid exit.

In some embodiments, the method comprises maintaining the liquid chlorine dioxide treatment solution at a temperature of at least 100° F. (37.8° C.), 105° F. (40.6° C.), 110° F. (43.3° C.) or 115° F. (46.1° C.).

In another aspect disclosed herein is a method of treating a target surface in need of decontamination using a recirculating chlorine dioxide treatment system, the method comprising (i) pumping liquid chlorine dioxide treatment solution containing a chlorine dioxide concentration disclosed herein (e.g., at least 5 ppm), to form flowing treatment solution (ii) passing flowing treatment solution through a first conduit containing baffles to create a laminar flow stream that flows (e.g., falls) downward under gravity from a liquid exit to form a curtain, (iii) contacting a target with the curtain, wherein the target is a surface in need of decontamination, (iv) collecting liquid chlorine dioxide treatment solution beneath the liquid exit and directing collected solution such that it recirculates through the first conduit and (v) adding chlorine dioxide to liquid chlorine dioxide treatment solution such that flowing treatment solution maintains the chlorine dioxide concentration.

In some embodiments, the method comprises assessing a chlorine dioxide concentration in the liquid chlorine dioxide treatment solution that flows through the recirculating loop. In some embodiments, the method comprises adjusting the amount of chlorine dioxide that is added based on the assessed chlorine dioxide concentration.

In some embodiments, the curtain is stable.

In some embodiments, a method disclosed herein is performed using a system that is disclosed herein, or with one or more components of such a system.

In some embodiments, the methods disclosed herein do not include steps or features that are not disclosed herein.

While this invention has been particularly shown and described with references to example embodiments thereof, it will be understood by those skilled in the art that various changes in form and details may be made therein without departing from the scope of the invention encompassed by the appended claims.

EXAMPLES

Example 1

In this example, two methods for applying a liquid chlorine dioxide treatment solution were compared with a chlorine dioxide treatment solution having the same volume and initial chlorine dioxide concentration, and using a system with the same delivery rate. One method was a curtain delivery method and the other method was a low-pressure spray method.

Experimental Setup

For both the methods a 330-gallon tote was used as the source fluid reservoir. The tote was filled with about 75 gallons of fresh water and also contained submersible sump-pump that provided the fluid flow to the system. A 6.6 gallon per minute (GPM) rotameter was in line between the pump and the chlorine dioxide delivery system that delivered a concentrated solution of chlorine dioxide (~1700 ppm) so as to make a liquid chlorine dioxide treatment solution containing an initial concentration (approximately 5 ppm) of chlorine dioxide. The delivery system sat over an aluminum sheet on a slight gradient, to provide a homogenous flow pathway of the treatment solution. The aluminum sheet allowed the treatment fluid to cascade back into the tote for recirculation. During experimentation, the rotameter was set to allow for approximately 4 GPM (about 13 L/min) of constant flow, achieved by slight pinching of a ball valve in line and downstream of the rotameter. The treatment solution was circulated through the system for a few minutes and if needed, additional concentrated solution was added to achieve the initial concentration (approximately 5 ppm chlorine dioxide) in the treatment solution before experimental runs commenced.

For the curtain application, a rain gutter was modified to serve as a trough for the fluid to fill into. The front wall of the trough was modified; it was slightly shorter and was rounded to achieve laminar or predominantly laminar flow of the fluid over the wall of the trough and down over the target belt (belt to be used for moving eggs or other products to be treated with the treatment solution). The trough also contained pieces of plastics filter media (a type of baffle) that converted the turbulent flow of the trough being filled to more homogenous, laminar flow allowing a sheer curtain or waterfall effect to be achieved consistently across the entire length of the trough, such that the curtain fell onto the target belt. The curtain had a thickness in the range of about 0.05 cm to 0.2 cm. The curtain was about 11" in height and approximately 2-2.5 feet wide.

For the spray application, a series of nozzles were used to apply the treatment solution.

Each application method was tested in multiple runs in which the liquid chlorine dioxide treatment solution was maintained at a particular target temperature (approximately 120° F. (this is the high temperature curtain or spray as referred to in Table 3) or a temperature of 60-75° F. (this is the low temperature curtain or spray as referred to in Table 3)).

Measurements and Results

For the curtain application method, the fluid was sampled at four locations: (A) from the hose that delivered treatment solution into the trough, (B) where the fluid entered the trough (C) within the trough near the exit where fluid flowed out of the trough to form the curtain, (D) where the fluid of the curtain fell onto the belt. For the spray application, the fluid was sampled at three locations: (A) from the hose that delivered treatment solution into the sprayer nozzle, (B) from the fluid as it exited the sprayer nozzle, (C) where the fluid of the spray fell onto the belt.

Chlorine dioxide concentrations were determined using the Palintest ChlordioX Plus device in accordance with the manufacturer's instructions.

The results are shown in the tables below.

Table 1 shows the results from the curtain application method.

TABLE 1

Results from Curtain Application Method

| Treatment fluid temperature range in ° F. | Ambient Temperature range in ° F. | Maximum Temperature Difference[1] in ° F. | Location | Average $ClO_2$ concentration in ppm (±STDEV) |
|---|---|---|---|---|
| 110-120 | 65-70 | 55 | A | 5.28 ± 0.59 |
| 110-120 | 65-70 | 55 | B | 4.70 ± 0.28 |
| 110-120 | 65-70 | 55 | C | 4.51 ± 0.52 |
| 110-120 | 65-70 | 55 | D | 3.34 ± 0.58 |
| 65-75 | 65-70 | 10 | A | 4.88 ± 0.87 |
| 65-75 | 65-70 | 10 | B | 4.91 ± 0.83 |
| 65-75 | 65-70 | 10 | C | 4.39 ± 0.79 |
| 65-75 | 65-70 | 10 | D | 3.51 ± 0.68 |

[1]This is the difference between the treatment fluid temperature and the ambient temperature.

Table 2 shows the results from the spray application method.

TABLE 2

Results from Spray Application Method

| Treatment fluid temperature range in ° F. | Ambient Temperature range in ° F. | Maximum Temperature Difference[1] in ° F. | Location | Average $ClO_2$ concentration in ppm (±STDEV) |
|---|---|---|---|---|
| 110-120 | 65-70 | 55 | A | 5.28 ± 0.58 |
| 110-120 | 65-70 | 55 | B | 3.57 ± 0.53 |
| 110-120 | 65-70 | 55 | C | 2.04 ± 0.45 |
| 60-70 | 65-70 | 10 | A | 4.86 ± 0.54 |
| 60-70 | 65-70 | 10 | B | 4.34 ± 0.71 |
| 60-70 | 65-70 | 10 | C | 3.43 ± 0.61 |

[1]This is the difference between the treatment fluid temperature and the ambient temperature.

Table 3 shows the comparative chlorine dioxide loss from the curtain and spray methods.

TABLE 3

Comparative Results of Curtain and Spray Application Methods

| Method | Average $ClO_2$ loss[1] in ppm (±STDEV) |
|---|---|
| Curtain with high temperature | 1.95 ± 0.58 |
| Spray with high temperature | 3.24 ± 0.67 |
| Curtain with low temperature | 1.37 ± 0.27 |
| Spray with low temperature | 1.44 ± 0.38 |

[1]The chlorine dioxide loss for the curtain application method was calculated as the chlorine dioxide concentration at location A minus the concentration at location D. The loss for the spray application method was calculated as the chlorine dioxide concentration at location A minus the concentration at location C.

These results indicate that applying chlorine dioxide with a curtain application method, as opposed to a spray application method, reduces the loss of chlorine dioxide and thereby improves chlorine dioxide delivery to the target surface. The beneficial effect of applying chlorine dioxide with the curtain application method was more pronounced when the high temperature treatment fluid was employed. The curtain application method has the advantages of less off-gassing and better treatment efficacy.

The invention claimed is:

1. A method comprising (i) forming a stable curtain of a liquid chlorine dioxide treatment solution that flows downward under gravity, and (ii) contacting a target surface in need of decontamination with the curtain.

2. The method of claim 1, comprising pumping liquid chlorine dioxide treatment solution through one or more baffles or laminar flow nozzles to form a laminar stream that passes through a liquid exit to form the curtain.

3. The method of claim 2, wherein the pumping is at a rate of about 1.5 GPM to 12 GPM per linear foot of width of the curtain.

4. The method of claim 1, wherein the curtain has a height of 0.1 to 0.3 m.

5. The method of claim 1, wherein the curtain has a depth of 0.05 cm to 1 cm.

6. The method of claim 1, wherein the method comprises maintaining the liquid chlorine dioxide treatment solution at a temperature of at least 100° F.

7. The method of claim 1, wherein the curtain of liquid chlorine dioxide treatment solution is at least 30° F. warmer than the ambient temperature and the ambient temperature is 50° F. to 90° F.

8. The method of claim 1, wherein contacting the target surface with the curtain comprises moving a target object under or through the curtain such that the liquid chlorine dioxide treatment solution runs over the target object.

9. The method of claim 1, wherein the treatment solution at a location where the curtain contacts the target surface retains at least 70% of a chlorine dioxide concentration that is initially present in the treatment solution at a location where it first forms the curtain.

10. A method comprising (i) pumping liquid chlorine dioxide treatment solution that initially comprises a chlorine dioxide concentration of at least 5 ppm through one or more baffles or laminar flow nozzles to achieve a laminar flow stream of treatment solution, (ii) directing the laminar flow stream such that it falls from a liquid exit to form a stable curtain that flows downward under gravity and (iii) contacting a target surface in need of decontamination with the curtain, wherein treatment solution at a location where the curtain contacts the target surface retains at least 70% of the chlorine dioxide concentration that is initially present in treatment solution that flows from the liquid exit.

11. The method of claim 10, wherein the pumping is at a rate of about 1.5 GPM to 12 GPM per linear foot of width (about 6 to 45 L/min per 0.3 m of width) of the curtain.

12. The method of claim 10, wherein the curtain has a height of 0.1 to 0.3 m.

13. The method of claim 10, wherein the curtain has a depth of 0.05 cm to 1 cm.

14. A method of forming a recirculating stable curtain of a liquid chlorine dioxide treatment solution to deliver chlorine dioxide to a target surface, the method comprising (i) forming a stable curtain of a liquid chlorine dioxide treatment solution that flows downward under gravity from a liquid exit, (ii) contacting a target surface in need of decontamination with the curtain, (iii) collecting liquid treatment solution that has flowed downwards through the curtain to make collected solution, (iv) introducing chlorine dioxide into collected solution and (v) recycling collected solution into which chlorine dioxide has been introduced by recirculating it through the liquid exit.

15. The method of claim 14, further comprising measuring a residual concentration of chlorine dioxide in the collected solution.

16. The method of claim 14, wherein the chlorine dioxide that is introduced into the collected solution is introduced at a dose that is effective to maintain a concentration of chlorine dioxide in the liquid chlorine dioxide treatment solution that flows through the liquid exit.

17. The method of claim 16, wherein the concentration is at least 2 ppm.

18. The method of claim 17, wherein the concentration is between 2 ppm and 50 ppm.

19. The method of claim 14, wherein contacting the target surface in need of decontamination with the curtain comprises moving a target object under or through the curtain such that the liquid chlorine dioxide treatment solution runs over the target object.

20. The method of claim 14, wherein the method comprises maintaining the liquid chlorine dioxide treatment solution at a temperature of at least 100° F.

21. The method of claim 14, wherein the treatment solution at a location where the curtain contacts the target surface retains at least 70% of the chlorine dioxide concentration that is present in the treatment solution that flows through the liquid exit.

22. The method of claim 14, comprising pumping liquid chlorine dioxide treatment solution to form a fluid flow that passes through one or more baffles or laminar flow nozzles to form a stream that flows laminarly and exits through the liquid exit to form the stable curtain.

23. A system for treating a target surface in need of decontamination with chlorine dioxide, the system comprising (i) a liquid chlorine dioxide treatment solution comprising an initial chlorine dioxide concentration of at least 5 ppm, (ii) a pump that pumps the liquid chlorine dioxide treatment solution to form a flowing treatment solution that flows through a first conduit, (iii) the first conduit, comprising baffles that remove turbulence and create laminar flow in flowing treatment solution, which flows through the first conduit to a liquid exit, (iv) the liquid exit, from which liquid chlorine dioxide treatment solution falls under gravity, forming a stable curtain that retains at least 70% of the initial chlorine dioxide concentration, and (v) a collecting conduit or container located beneath the curtain, which catches treatment solution.

24. The system of claim 23, comprising a target surface in need of decontamination located less than 0.3 m beneath the liquid exit such that the target surface is contacted by the curtain.

25. The system of claim 23, comprising a conveyor belt that moves objects in need of decontamination through the curtain.

26. A recirculating system for treating a target surface in need of decontamination with chlorine dioxide, the system comprising (i) a liquid chlorine dioxide treatment solution containing a chlorine dioxide concentration of at least 5 ppm, (ii) a pump that pumps the liquid chlorine dioxide treatment solution to form a flowing treatment solution that flows through a first conduit, (iii) the first conduit, comprising baffles that remove turbulence in flowing treatment solution that flows through the first conduit and a liquid exit from the first conduit, (iv) the liquid exit, from which liquid chlorine dioxide treatment solution flows downward under gravity, forming a stable curtain, (v) a collecting conduit, located beneath the liquid exit, which collects treatment solution, (vi) a connecting conduit for recirculating treatment solution, the connecting conduit funneling treatment solution from the collecting conduit back into the first conduit, and (vii) chlorine dioxide introduction apparatus that introduces chlorine dioxide into liquid chlorine dioxide treatment solution so as to maintain said chlorine dioxide concentration of at least 5 ppm in liquid chlorine dioxide treatment solution that flows from the liquid exit.

27. The system of claim 26, comprising a heater that heats the flowing treatment solution to maintain it at a temperature of at least 100° F.

* * * * *